US00PP34373P2

(12) United States Plant Patent
Kordes

(10) Patent No.: US PP34,373 P2
(45) Date of Patent: Jun. 28, 2022

(54) MINIATURE ROSE PLANT NAMED 'KORAROMA13'

(50) Latin Name: *Rosa hybrida*
Varietal Denomination: 'KORaroma13'

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 17/565,642

(22) Filed: Dec. 30, 2021

(51) Int. Cl.
*A01H 6/74* (2018.01)
*A01H 5/02* (2018.01)

(52) U.S. Cl.
USPC ..... Plt./122

(58) Field of Classification Search
USPC ..... Plt./122
See application file for complete search history.

(56) References Cited

U.S. PATENT DOCUMENTS

PP30,420 P3 4/2019 Kordes

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORaroma13', is described. The new variety forms in abundance on a substantially continuous basis attractive, crimson red colored blossoms. The vegetation is vigorous, and the growth habit is compact. Attractive dark green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORaroma13'.

BACKGROUND OF THE INVENTION

The new variety of miniature rose plant of the present invention was created by controlled breeding in 2018 at Offenseth-Sparrishoop, Germany by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) of the new variety was a different unnamed breeder seedling (not patented).

The parentage of the new variety can be summarized as follows:

unnamed breeder seedling x different unnamed breeder seedling

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) abundantly and substantially continuously forms attractive, crimson red colored blossoms,
(b) exhibits a compact growth habit,
(c) forms vigorous vegetation, and
(d) forms attractive ornamental matte foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed seedling seed parent displays a weaker flower fragrance and provides a less compact growth habit compared to the new variety. Additionally, the different unnamed seedling pollen parent displays a stronger flower fragrance and provides a lower petal count compared to the new variety. Moreover, the new variety can be readily distinguished from non-parental related similar varieties. For example, 'KORaroma07' (U.S. Plant Pat. No. 30,420) displays pink colored flowers and provides a stronger flower fragrance compared to the crimson red colored flowers of new variety.

The new variety has been named the 'KORaroma13' variety.

The first sale or first offer for sale of the new variety was January 2021 in Germany by the inventor or by another who obtained the new variety directly or indirectly from the inventor.

BRIEF DESCRIPTION OF THE PHOTOGRAPH

The accompanying photograph shows, as nearly true as it is reasonably possible to make the same in a color illustration of this character, a typical specimen of the new variety and blossoms of the new variety. The illustrated rose plant of the new variety was approximately twelve weeks of age and was grown indoors in a 10.5 cm container on its own roots at Odense, Denmark.

The drawing sheet illustrates a specimen of the plant displaying flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on a one-year-old specimen of the new variety, observed during October, while growing on its own roots in a greenhouse in a one-gallon container in Cochranville, Pa.

Botanical classification: *Rosa hybrida* cultivar KORaroma13.

Commercial classification: Miniature Rose.

Plant:

*Height*.—Approximately up to 32.0 cm.

*Width*.—Approximately up to 30.0 cm.

*Habit*.—Compact.

Branches:

*Stem color*.—Commonly near Green Group 143A.

*Length*.—Main stems: approximately 30.0 cm on average. — secondary stems: approximately 9.0 cm on average.

*Texture*.—Glabrous.

*Thorns*.—Amount: moderate. — young thorns: length is approximately 3.0 mm on average; width is approximately 2.0 mm at point of attachment; and color is commonly near Orange Group 26C.

Leaflets:

*Number*.—3, 5, and 7.

*Shape*.—Ovate; apex shape is acute; and base shape is rounded.

*Arrangement*.—Odd-pinnate.

*Venation pattern*.—Reticulate.

*Margin*.—Serrate.

*Glossiness of upper side*.—Matte.

*Texture*.—Upper surface: smooth. — under surface: smooth.

*Size*.—Terminal leaflet: length is approximately 4.5 cm on average; width is approximately 2.2 cm on average. — lower leaflets: length is approximately 2.6 cm on average; width is approximately 1.2 cm on average. — 5-Leaflet leaf: length is approximately 8.0 cm on average; width is approximately 6.0 cm on average.

Foliage:

*Young foliage*.—Upper surface color: commonly near Green Group 137A with indistinguishable venation. — under surface color: commonly a blend of near Yellow-Green Group 147B and Greyed-Orange Group 176C with venation commonly near Yellow-Green Group 146C.

*Old foliage*.—Upper surface color: commonly near Green Group 136A with indistinguishable venation. — under surface color: commonly near Yellow-Green Group 147B with venation commonly near Green Group 139C.

*Petiole*.—Texture: upper surface is smooth; under surface is mostly smooth with sparse prickles. — upper surface color: commonly near Green Group 137A. — under surface color: commonly near Green Group 137B.

*Rachis*.—Upper surface color: commonly near Green Group 137A. — under surface color: commonly near Green Group 137B.

*Stipules*.—Length: approximately 7.0 mm on average. — width: approximately 2.0 mm on average. — margin: Entire to erose. — upper surface color: commonly near Green Group 137A. — lower surface color: commonly near Green Group 138B.

Inflorescence:

*Number of flowers*.—About 7 blooms on average on a plant at once.

*Number of blossoms per stem or in a cluster*.—Typically 1 and 3 blooms per stem on average.

*Peduncle*.—Color: commonly near Green Group 138A. — diameter: approximately 3.0 mm on average. — length: approximately 3.0 cm on average. — surface texture: glabrous. — strength: strong.

*Sepals*.—Number: 5. — upper surface color and texture: commonly near Green Group 138A, covered in short pubescence. — under surface color and texture: commonly near Green Group 138A, puberulent. — size: length is approximately 1.5 cm on average; width is approximately 0.5 cm on average. — margin: entire with extension on two or three sepals measuring 1.0 cm in length and 3.0 mm in width. shape: lanceolate. — apex: acute to aristate. — base: truncate or flat as it joins the receptacle.

*Buds*.—Shape: globular. — size: length is approximately 2.0 cm on average; width is approximately 2.0 cm on average. — color (when opening): commonly near Red-Purple Group 62C.

*Flower*.—Form: double, cuplike. — profile: flat. — diameter: approximately 6.0 cm on average. — height: approximately 2.5 cm on average. — duration: on the plant approximately 23 days. — petal color when first and fully opened: upper surface is commonly near Red Group 47A with a basal spot of near Red Group 53A; under surface is commonly near Red Group 47B with basal spot of near Red Group 53A. — petal color when fading: upper and under surfaces are commonly near Purple Group 79B with hint of Red Group 47A. — petal texture of upper and lower surfaces: glabrous.

*Fragrance*.—Medium sweet scent.

*Petal*.—Number: 36 on average. — drop: average for the type. — length: inner petals are approximately 1.0 cm on average and outer petals are approximately 2.5 cm on average. — width: inner petals are approximately 8.0 mm on average and outer petals are approximately 2.5 cm on average. — overall shape: broadly obovate. — margin: entire. — apex shape: rounded to cuspidate. — base shape: rounded to cuneate.

*Petaloids*.—Number: commonly 5 per flower. — color upper and under surfaces: commonly near Red Group 47A with a basal spot of near Yellow Group 4D. — length: approximately 5.0 mm on average. — width: approximately 3.0 mm on average. — texture: smooth. — margins: variable, entire to erose. — shape: rounded and mostly curving inward. — apex: round. — base: cuneate.

*Stamen*.—Number: approximately 80. — anthers: number is approximately 80; color is commonly near Yellow Group 11C; length is approximately 1.5 mm on average; and shape is oval. — filaments: length is approximately 1.5 mm on average and color is commonly near Green-Yellow Group 1B.

*Pistils*.—Arrangement: separate and free. — number: approximately 96. — style: length is approximately 5.0 mm and color is commonly near Yellow Group 11C at the base, transitioning to near Red Group 39A at the apex. — stigma: diameter is commonly less than 1.0 mm; shape is fan shaped; and color is commonly near Green-Yellow Group 1B.

*Receptacle*.—Diameter: approximately 8.0 mm on average. — shape: urn shaped. — color: commonly near Yellow-Green Group 144A. — surface texture: smooth.

*Pollen*.—None observed.

*Hips/seed*.—None observed.

Development:

*Vegetation*.—Dark green, vigorous, and strong.

*Blossoming*.—Abundant and substantially continuous.

*Resistance to diseases*.—Good resistance for powdery mildew (*Sphaerotheca pannosa*) disease under normal greenhouse growing conditions in Cochranville, Pa.

*Hardiness*.—Unknown.

The new 'KORaroma13' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORaroma13' characterized by the following combination of characteristics:

(a) abundantly and substantially continuously forms attractive, crimson red colored blossoms, (b) exhibits a compact growth habit, (c) forms vigorous vegetation, and (d) forms attractive ornamental matte foliage;

substantially as herein shown and described.

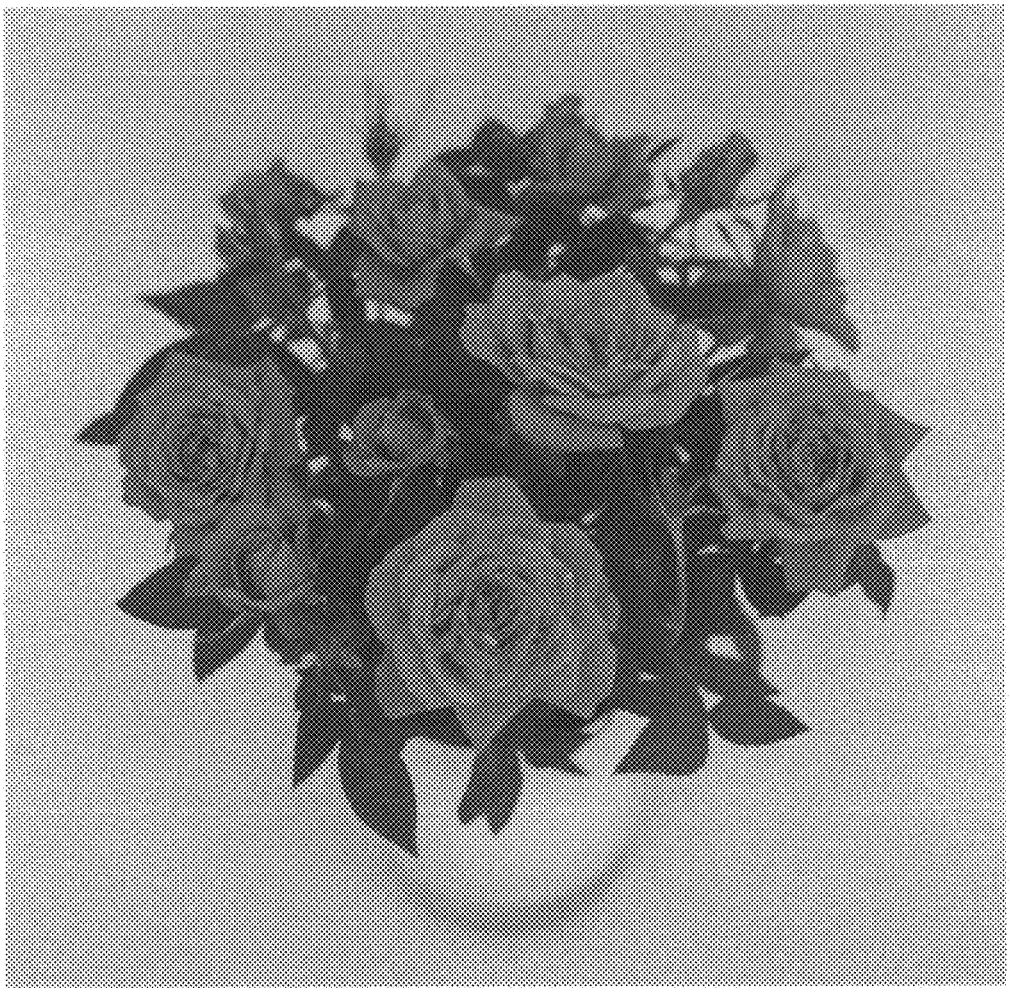

* * * * *